US012690766B2

(12) United States Patent
Yukimori et al.

(10) Patent No.: US 12,690,766 B2
(45) Date of Patent: Jul. 28, 2026

(54) OPHTHALMOLOGIC APPARATUS

(71) Applicant: TOPCON CORPORATION, Tokyo (JP)

(72) Inventors: Takafumi Yukimori, Tokyo (JP); Makoto Saika, Tokyo (JP); Yoko Tatara, Tokyo (JP); Akio Hayashi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 332 days.

(21) Appl. No.: 18/126,447

(22) Filed: Mar. 26, 2023

(65) Prior Publication Data

US 2023/0309822 A1      Oct. 5, 2023

(30) Foreign Application Priority Data

Mar. 29, 2022    (JP) ................................. 2022-053984

(51) Int. Cl.
| | |
|---|---|
| *A61B 3/032* | (2006.01) |
| *A61B 3/00* | (2006.01) |
(Continued)

(52) U.S. Cl.
CPC .......... *A61B 3/0325* (2013.01); *A61B 3/0008* (2013.01); *A61B 3/0016* (2013.01);
(Continued)

(58) Field of Classification Search
CPC ... A61B 3/0008; A61B 3/0016; A61B 3/0025; A61B 3/0005; A61B 3/0041; A61B 3/02;
(Continued)

(56) References Cited

U.S. PATENT DOCUMENTS

| | | | |
|---|---|---|---|
| 5,777,718 | A | 7/1998 | Kohayakawa |
| 5,844,661 | A | 12/1998 | Uchida |
(Continued)

FOREIGN PATENT DOCUMENTS

| | | | |
|---|---|---|---|
| CN | 113208884 A | 8/2021 | |
| EP | 3175776 A1 | 7/2017 | |
(Continued)

OTHER PUBLICATIONS

European Search Report from corresponding European Application No. EP23164349, mailed on Jul. 28, 2023, 7 pages.
(Continued)

*Primary Examiner* — Jason M Mandeville
(74) *Attorney, Agent, or Firm* — Tucker Ellis LLP

(57) ABSTRACT

An ophthalmologic apparatus includes a subjective measurement optical system configured to measure a subjective refractive value of a subject eye, an objective measurement optical system configured to measure objective refractive characteristics of the subject eye, and a controller configured to control the subjective measurement optical system and the objective measurement optical system. The controller is further configured to measure the objective refractive characteristics of the subject eye by the objective measurement optical system and perform objective monitoring to monitor objective measurement information obtained by the measurement of the objective refractive characteristics during an RG test for checking whether or not corrected power is overcorrected or undercorrected by the subjective measurement optical system.

15 Claims, 10 Drawing Sheets

(51) Int. Cl.
| | |
|---|---|
| *A61B 3/02* | (2006.01) |
| *A61B 3/028* | (2006.01) |
| *A61B 3/10* | (2006.01) |
| *A61B 3/103* | (2006.01) |

(52) U.S. Cl.
CPC .......... *A61B 3/0025* (2013.01); *A61B 3/0041* (2013.01); *A61B 3/02* (2013.01); *A61B 3/028* (2013.01); *A61B 3/032* (2013.01); *A61B 3/10* (2013.01); *A61B 3/103* (2013.01)

(58) Field of Classification Search
CPC ....... A61B 3/028; A61B 3/032; A61B 3/0325; A61B 3/10; A61B 3/103

USPC .......................................................... 351/205
See application file for complete search history.

(56) References Cited

U.S. PATENT DOCUMENTS

| | | | |
|---|---|---|---|
| 5,859,688 A | 1/1999 | Hosoi | |
| 5,929,971 A | 7/1999 | Hosoi | |
| 5,956,121 A | 9/1999 | Hosoi | |
| 10,966,604 B2 * | 4/2021 | Takii | A61B 3/0008 |
| 2005/0018132 A1 | 1/2005 | Fukuma | |
| 2005/0174535 A1 * | 8/2005 | Lai | A61B 3/1015 |
| | | | 351/205 |
| 2005/0264760 A1 | 12/2005 | Ikezawa | |
| 2009/0303439 A1 | 12/2009 | Kawai | |
| 2011/0228225 A1 | 9/2011 | Liang | |
| 2013/0208244 A1 | 8/2013 | Sakagawa | |
| 2014/0218685 A1 * | 8/2014 | Nakamura | A61B 3/0091 |
| | | | 351/221 |
| 2018/0064339 A1 | 3/2018 | Takii et al. | |
| 2019/0099073 A1 | 4/2019 | Takii | |
| 2022/0095910 A1 | 3/2022 | Horino et al. | |

FOREIGN PATENT DOCUMENTS

| | | | |
|---|---|---|---|
| GB | 2355540 | A | 4/2001 |
| JP | H06197868 | A | 7/1994 |
| JP | H06233741 | A | 8/1994 |
| JP | H0910175 | A | 1/1997 |
| JP | H0994223 | A | 4/1997 |
| JP | H11113848 | A | 4/1999 |
| JP | H11346997 | A | 12/1999 |
| JP | 4330399 | B2 | 9/2009 |
| JP | 2010082252 | A | 4/2010 |
| JP | 2015029527 | A | 2/2015 |
| JP | 2018038788 | A | 3/2018 |
| JP | 2018042760 | A | 3/2018 |
| JP | 2018143585 | A | 9/2018 |
| JP | 2020031827 | A | 5/2020 |
| JP | 6733160 | B2 | 7/2020 |
| JP | 6828234 | B | 2/2021 |
| JP | 2021065669 | A | 4/2021 |
| WO | 2021049314 | A1 | 3/2021 |

OTHER PUBLICATIONS

European Search Report from corresponding European Application No. 23164371, mailed on Aug. 1, 2023, 7 pages.
European Search Report from corresponding European Application No. 23164359.4 mailed on Aug. 1, 2023, 10 pages.
Carlo Aleci et al.: "The optokinetic response is effective to assess obje ctive visual acuity in patients with cataract and age related macular degeneration"; Int Ophthalmol, Published on Aug. 14, 2018, 10 pages.
Japanese Office Action from corresponding Application No. 2022-053982 mailed on Nov. 4, 2025, 9 pages with translation.
Japanese Office Action from corresponding Application No. 2022-053983 mailed on Nov. 4, 2025, 8 pages with translation.
Japanese Office Action from corresponding Application No. 2022-053984 mailed on Nov. 25, 2025, 6 pages with translation.
Japanese Decision to Grant from corresponding Application No. 2022-053982, mailed on Jan. 20, 2026, 3 pages with translation.

* cited by examiner

OBJECTIVE
MEASUREMENT
VALUE
(SPHERICAL
EQUIVALENT)

AMOUNT OF FOG

———————— FIRST EXAMINEE
---------- SECOND EXAMINEE
—·—·—·— THIRD EXAMINEE

OPHTHALMOLOGIC APPARATUS

CROSS-REFERENCE TO RELATED APPLICATION

The present application is based on and claims priority to Japanese Patent Application No. 2022-053984 filed on Mar. 29, 2022, the disclosure of which is hereby incorporated by reference in its entirety.

FIELD OF THE INVENTION

The present disclosure relates to an ophthalmologic apparatus.

BACKGROUND

There is a conventionally known ophthalmologic apparatus in which monocular measurement starts in response to fogging (or applying fog) to an eye to be examined (also referred to as subject eye hereinafter). For example, with an examinee or subject having both eyes fogging, an examiner operates a controller to release the fogging from one of the eyes to be examined and sets the weakest power enabling maximum vision. After that, tests such as a duo-chrome test for preventing excessive correction and a cross-cylinder test (cylindrical axis test and cylindrical power test) are carried out, and then the maximum monocular visual acuity value is verified based on a visual acuity test (e.g., see JP6828234B2). Hereinafter, such a duo-chrome test is referred to as an "RG test".

In a subjective examination, at the time of the RG test for checking whether or not corrected power is excessive in correction (overcorrected) or low in correction (undercorrected), the accommodation function of focusing of the crystalline lens of the examination-target eye or subject eye is regarded as relaxed, and it is checked whether or not corrected power is overcorrected or undercorrected. However, during the RG test, for example, in a case where the subject eye has difficulty in doing fixation due to examination fatigue or in a case where the subject eye keeps gazing at the red optotype side of an RG chart, the accommodation function of the subject eye is likely to intervene. Therefore, direct use of a test result from the RG test, in which the accommodation intervention by the subject eye has occurred, causes a deterioration in the accuracy of checking the corrected power based on the RG test. According to the conventional technology disclosed in JP6828234B2, it is difficult to determine or verify whether or not the accommodation intervention by the subject eye has occurred at the time of the RG test.

The present disclosure has been made by considering the above problem. An object of the present disclosure is to provide an ophthalmologic apparatus enabling determination of whether or not the accommodation intervention by a subject eye has occurred at the time of an RG test.

SUMMARY

To achieve the object, an ophthalmologic apparatus includes a subjective measurement optical system configured to measure a subjective refractive value of a subject eye, an objective measurement optical system configured to measure objective refractive characteristics of the subject eye, and a controller configured to control the subjective measurement optical system and the objective measurement optical system. The controller is further configured to measure the objective refractive characteristics of the subject eye by the objective measurement optical system and to perform objective monitoring to monitor objective measurement information obtained by the measurement of the objective refractive characteristics during an RG test for checking whether or not corrected power is overcorrected or undercorrected by the subjective measurement optical system.

DETAILED DESCRIPTION

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

An ophthalmologic apparatus according to a first embodiment of the present disclosure will be described below with reference to the accompanying drawings.

The ophthalmologic apparatus 1 according to the first embodiment is a binocular open-field type apparatus enabling simultaneous measurement of eye characteristics (ocular characteristics) of both eyes of an examinee or subject with the left and right eyes open. The ophthalmologic apparatus 1 may measure the eye characteristics of each of the eyes by occluding the eye or turning off a fixation target.

Figure 1:
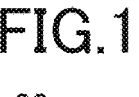
FIG. 1 is a perspective view of the entire configuration of an ophthalmologic apparatus according to a first embodiment.

The configuration of the ophthalmologic apparatus 1 will be described with reference to FIG. 1. As illustrated in FIG. 1, the ophthalmologic apparatus 1 includes a support base 10, a measurement portion 20, an examiner controller 30, and a controller 40. FIG. 1 shows X, Y, and Z directions. Hereinafter, a left-right direction is defined as the X direction, an up-down direction (vertical direction) is defined as the Y direction, and a direction (depth direction) orthogonal to the X and Y directions is defined as the Z direction. The directions are defined as seen from the examiner.

The measurement portion 20 includes a support base 10. The support base 10 includes a pillar 11 placed on the floor and an eye examination table 12 supported by the pillar 11. The eye examination table 12 is used to place devices such as the examiner controller 30 or tools used during the eye examination and support the posture of the examinee. The position in the Y direction (height) of the eye examination table 12 may be fixed or may be supported by the pillar 11 to be adjustable in the Y direction.

The measurement portion 20 includes an arm 21, a measurement head 22, and a forehead receiver 23. The arm 21 extends in the Z direction from the pillar 11 to a first side, which is an examinee side. The arm 21 has an end supported at the leading end of the pillar 11 and the other end to which the measurement head 22 is attached. Thus, the measurement head 22 is suspended from the pillar 11 via the arm 21 above the eye examination table 12. The arm 21 is movable in the Y direction with respect to the pillar 11. The arm 21 may be movable in the X direction and/or the Z direction with respect to the pillar 11.

The measurement head 22 is configured to measure the eye characteristics of subject eyes E. The measurement head 22 includes a driver 22a, a left measurement portion 22L, and a right measurement portion 22R. The left measurement portion 22L and the right measurement portion 22R are provided below the driver 22a and arranged in the X direction. The left measurement portion 22L and the right measurement portion 22R are paired to correspond to the left and right eyes of the examinee, respectively. The left measurement portion 22L includes a left measurement optical system 25L that is configured to measure the eye characteristics of the left eye of the examinee as the subject eye E (left subject eye). The right measurement portion 22R includes a right measurement optical system 25R that is configured to measure the eye characteristics of the right eye of the examinee as the subject eye E (right subject eye). A measurement result from the measurement head 22 is input to the controller 40.

The driver 22a is a mechanism that is configured to individually drive the left measurement portion 22L and the right measurement portion 22R to move horizontally (in X direction), move vertically (in Y direction), rotate about the X-direction axis, and rotate about the Y-direction axis.

The ophthalmologic apparatus 1 serves as an objective measuring machine having a subjective function and including a subjective measurement optical system, an objective measurement optical system, a phoropter, and an eye chart. The ophthalmologic apparatus 1 can perform the objective and subjective measurements of the eye characteristics of the subject eye E. That is, the examiner can carry out the objective examination and the subjective examination with the ophthalmologic apparatus 1. In the objective examination, the subject eye E is irradiated with light and then information regarding the subject eye E (eye characteristics thereof) is measured based on the detection result of the reflected light.

The objective examination includes the measurement for the acquisition of the eye characteristics of the subject eye E and photographing or capturing for the acquisition of an image of the subject eye E. For example, the objective examination includes refractive power measurement (refraction measurement), cornea shape measurement (kerato-measurement), eye pressure measurement, fundus photography or fundus shooting, photographing with optical coherence tomography (OCT photographing), measurement with OCT, and the like. In the subjective examination, the examinee is presented with the optotype, the eyechart, or the like, and then, the information regarding the subject eye E (eye characteristics) is measured based on the examinee's response to the presented optotype, the eyechart, or the like. For example, the subjective examination includes the subjective refraction measurements such as a far-point examination, a mid-point examination, a near-point examination, a contrast test, a glare test, a visual field test, and the like.

Figure 2:
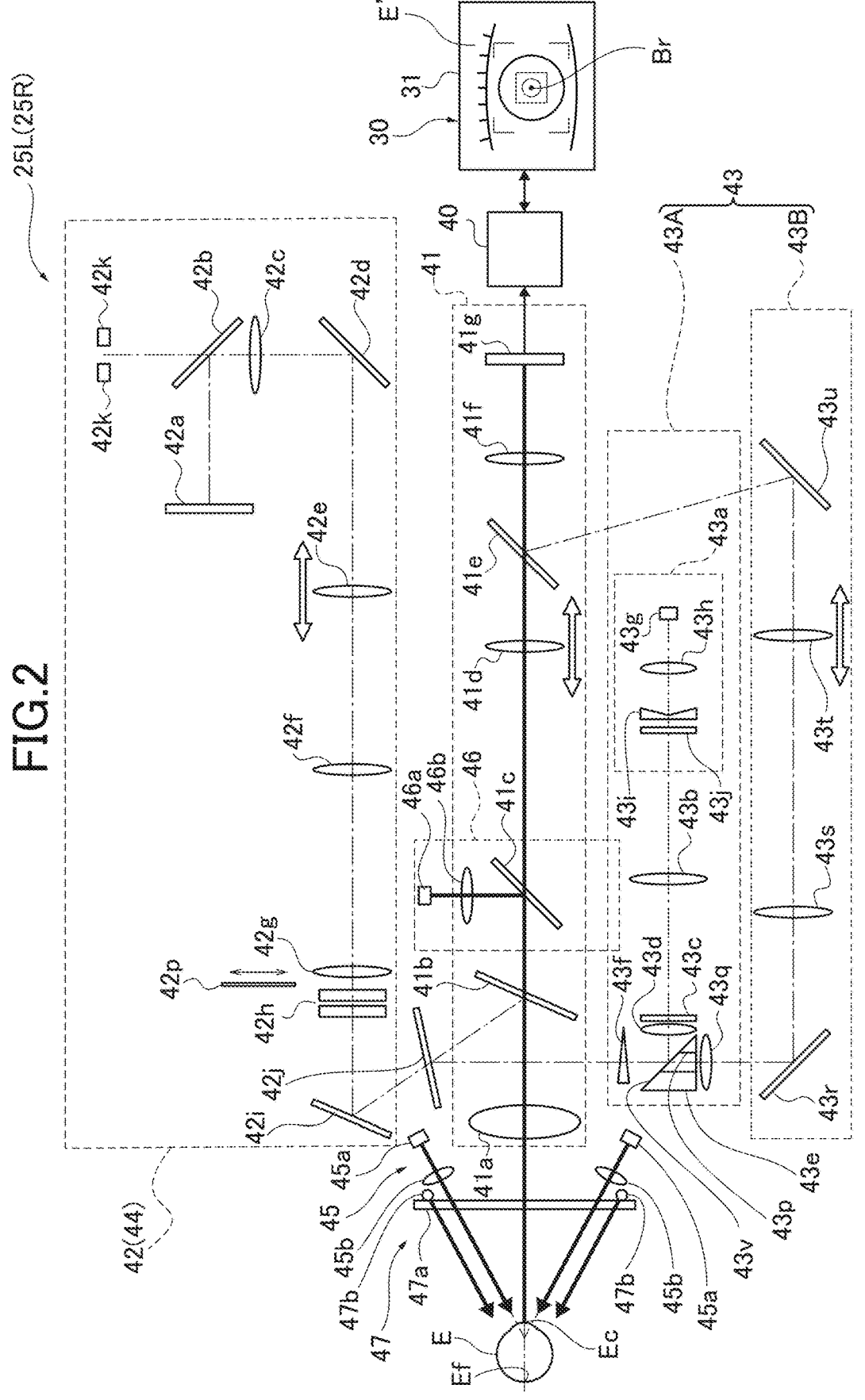
FIG. 2 illustrates a detailed configuration of a left measurement optical system of the ophthalmologic apparatus according to the first embodiment.

Therefore, as illustrated in FIG. 2, each of the left measurement optical system 25L and the right measurement optical system 25R in the measurement head 22 includes an observation system 41 that observes the anterior ocular segment of the subject eye E, an optotype projection system 42 that presents the optotype to the subject eye E, a refraction measurement system 43 and a keratometry (kerato) measurement system (also referred to as kerato-measurement system hereinafter) 47 (left-eye objective measurement optical system or right-eye objective measurement optical system) that measure the eye characteristics of the subject eye E, and the like. The detailed configurations of the left measurement optical system 25L and the right measurement optical system 25R will be described below.

The forehead receiver 23 is provided in the measurement portion 20 and is disposed between the left measurement portion 22L and the right measurement portion 22R. The forehead receiver 23 receives a part of the face (i.e., forehead) of the examinee to support the face of the examinee in contact with during measurement of the eye characteristics. That is, the examinee in front of the eye examination table 12 places his or her forehead on the forehead receiver 23 and holds the face in a stable orientation or position. The position of the forehead receiver 23 is adjustable by moving the arm 21 in the Y direction with respect to the pillar 11.

The examiner controller 30 is an information processing device that is configured to receive an input operation from the examiner and output a control signal to the controller 40. The examiner controller 30 is, for example, a tablet terminal, a smartphone, or the like. The examiner controller 30 is removable from the measurement portion 20 to be carried by the examiner. The examiner controller 30 may be a laptop or desktop personal computer or may be a dedicated controller for the ophthalmologic apparatus 1. The examiner controller 30 exchanges information with the controller 40 via wireless communication or network communication.

The examiner controller 30 includes a display 31 as illustrated in FIG. 1, an operation-side controller (not illustrated), and an input button (not illustrated). The display 31 consists of a touch panel display provided on the examiner controller 30, and the input button is set on the screen display. The operation-side controller consists of a microcomputer in the examiner controller 30. The operation-side controller controls an image to be displayed on the display 31 based on the measurement result or detection result transmitted from the controller 40. The operation-side controller outputs, to the controller 40, a control signal responsive to an operation to the input button.

The controller 40 is an information processing device provided below the eye examination table 12. Based on control signals transmitted from the examiner controller 30, the controller 40 controls, in a centralized manner, each part of the measurement portion 20 including the left measurement optical system 25L and the right measurement optical system 25R, each including the objective measurement optical system (refraction measurement system 43 and kerato-measurement system 47), the optotype projection system 42, and the like. The controller 40 transmits, to the examiner controller 30, the measurement results of the eye characteristics of the subject eye E measured by the measurement head 22.

Next, the detailed configurations of the left measurement optical system 25L and the right measurement optical system 25R will be described with reference to FIG. 2. The left measurement optical system 25L and the right measurement optical system 25R have the same configuration. Accordingly, only the left measurement optical system 25L will be described while the description of the right measurement optical system 25R is omitted.

As illustrated in FIG. 2, the left measurement optical system 25L includes the observation system 41, the optotype projection system 42, a subjective measurement optical system 44, a first alignment system 45, a second alignment system 46, and the refraction measurement system 43 and the kerato-measurement system 47 as the examples of the objective measurement optical system. Each of the subjective measurement optical system 44, the refraction measurement system 43, and the kerato-measurement system 47 is a measurement optical system that is configured to measure the eye characteristics of the subject eye E.

The observation system 41 includes an objective lens 41a, a first dichroic filter 41b, a first half mirror 41c, a first relay lens 41d, a second dichroic filter 41e, an image-forming lens 41f, and an imaging element (e.g., CCD) 41g.

The observation system 41 forms an image of a light flux reflected by the subject eye E (anterior ocular segment) on the imaging element 41g by the image-forming lens 41f via the objective lens 41a. As a result, on the imaging element 41g, a keratometry (kerato) ring light flux, a light flux of a first alignment light source 45a, and a light flux (bright spot image Br) of a second alignment light source 46a, which are described later, are projected to form an anterior-ocular-segment image E. The imaging element 41g captures the anterior-ocular-segment image E and acquires an image signal of the anterior-ocular-segment image E. The controller 40 displays, on the display 31 of the examiner controller 30, the anterior-ocular-segment image E or the like based on the image signal from the imaging element 41g.

The kerato-measurement system 47 is provided ahead of the objective lens 41a. The kerato-measurement system 47 is an example of the objective measurement optical system. The kerato-measurement system 47 is configured to measure the cornea shape (radius of curvature) of the subject eye E.

The kerato-measurement system 47 includes a kerato-plate 47a and a kerato-ring light source 47b. The kerato-plate 47a is a plate provided with a concentric slit about the optical axis of the observation system 41 and is provided near the objective lens 41a. The kerato-ring light source 47b is provided to correspond to the slit of the kerato-plate 47a.

In the kerato-measurement system 47, the light flux from the kerato-ring light source 47b in lighting passes through the slit of the kerato-plate 47a, so that a kerato-ring light flux for measurement of the cornea shape (ring-shaped optotype for measurement of cornea curvature) is projected onto the subject eye E (cornea Ec). After reflected on the cornea Ec of the subject eye E, the kerato-ring light flux forms an image on the imaging element 41g by the observation system 41. Thus, the imaging element 41g receives and/or detects the ring-shaped image of the kerato-ring light flux. The controller 40 displays, on the display 31, the image of the kerato-ring light flux detected by the imaging element 41g. Furthermore, the controller 40 measures the cornea shape (radius of curvature) of the subject eye E based on an image signal detected by the imaging element 41g.

The first alignment system 45 is provided behind the kerato-measurement system 47 (kerato-plate 47a). The first alignment system 45 is configured to position or align the optical system relative to the subject eye E in the direction along the optical axis of the observation system 41 (front-back direction or Z direction). The first alignment system 45 includes a pair of first alignment light sources 45a and a pair of first projection lenses 45b.

In the first alignment system 45, the light flux from each of the first alignment light sources 45a is made to the parallel light flux by the corresponding first projection lens 45b. Then, the parallel light flux is projected onto the cornea Ec of the subject eye E through an alignment hole provided at the kerato-plate 47a.

Based on the bright spot (bright-spot image Br) projected on the cornea Ec, the controller 40 or the examiner moves the left measurement portion 22L (or right measurement portion 22R) in the front-back direction to perform the alignment in the direction along the optical axis of the observation system 41 (front-back direction). During the alignment in the front-back direction, the controller 40 or the examiner adjusts the position of the left measurement portion 22L (or right measurement portion 22R) such that the ratio between the interval between two spot images by the first alignment light sources 45a and the diameter of the kerato-ring image on the imaging element 41g falls within a predetermined range.

The observation system 41 is provided with the second alignment system (parallel optical system) 46. The second alignment system 46 is configured to position or align the optical system relative to the subject eye E in the directions orthogonal to the optical axis of the observation system 41 (up-down and left-right directions, i.e., Y and X directions). The second alignment system 46 includes the second alignment light source 46a and a second projection lens 46b. The second alignment system 46 shares the first half mirror 41c, the first dichroic filter 41b, and the objective lens 41a with the observation system 41.

In the second alignment system 46, the light flux from the second alignment light source (point light source) 46a is made to the parallel light flux through the objective lens 41a. Then, the parallel light flux is projected onto the cornea Ec of the subject eye E. The parallel light flux projected from the second alignment system 46 onto the cornea Ec of the subject eye E forms a bright spot of the alignment light at a substantially middle position between the cornea apex and the center of curvature of the cornea Ec.

Based on the bright spot (bright-spot image Br) projected on the cornea Ec, the controller 40 or the examiner moves the left measurement portion 22L (or right measurement portion 22R) in the up-down direction or the left-right direction to perform the alignment in the directions (up-down and left-right directions) orthogonal to the optical axis of the observation system 41.

The optotype projection system 42 projects an optotype (fixation target), leading to presentation to the fundus Ef of the subject eye E to bring the subject eye E into fixation or fogging. The subjective measurement optical system 44 projects the optotype onto the subject eye E during the subjective examination. In the ophthalmologic apparatus 1, the optotype projection system 42 and the subjective measurement optical system 44 share the optical elements in the optical system.

The optotype projection system 42 (subjective measurement optical system 44) includes a display 42a, a second half mirror 42b, a second relay lens 42c, a first reflective mirror 42d, a first focusing lens 42e, a third relay lens 42f, a first field lens 42g, a variable cross-cylinder lens (also referred to as VCC hereinafter) 42h, a second reflective mirror 42i, and a third dichroic filter 42j. The optotype projection system 42 (subjective measurement optical system 44) shares the first dichroic filter 41b and the objective lens 41a with the observation system 41. Furthermore, the optotype projection system 42 (subjective measurement optical system 44) includes at least two glare light sources 42k that irradiate the subject eye E with glare light, around the optical axis and on an optical path different from the optical path to the display 42a for the subjective examination.

The display 42a displays the fixation target or the point-like optotype as the optotype for fixing a line of sight for the objective examination and for fogging to the subject eye E and displays the subjective-examination optotype for the subjective examination of the eye characteristics of the subject eye E (e.g., visual acuity value, far-point power, and near-point power). The display 42a may be an organic electroluminescence (EL) display or a liquid crystal display (LCD). The display 42a displays any image in response to the control of the controller 40. The display 42a is provided at a position conjugate with the fundus Ef of the subject eye E on the optical path of the optotype projection system 42 (subjective measurement optical system 44).

The first focusing lens 42e moves forward or backward along the optical axis by a drive motor (not illustrated) controlled by the controller 40. The controller 40 moves the first focusing lens 42e toward the subject eye E, so that the refractive index can be displaced to the negative side. The controller 40 moves the first focusing lens 42e in the direction away from the subject eye E, so that the refractive index can be displaced to the positive side (for far view direction). Therefore, the controller 40 changes the presentation position of the optotype displayed on the display 42a by the forward or backward movement of the first focusing lens 42e, so that the examination distance is changed from the presentation position of the optotype to the subject eye E.

The optotype projection system 42 (subjective measurement optical system 44) includes a pinhole plate 42p at a position substantially conjugate with the pupil of the subject eye E on the optical path (between first field lens 42g and VCC 42h in example of FIG. 2). The pinhole plate 42p is formed of a plate member provided with a through-hole. The pinhole plate 42p is controlled by the controller 40 to be inserted into or removed from the optical path of the optotype projection system 42 (subjective measurement optical system 44). The through-hole is located on the optical axis when the pinhole plate 42p is inserted in the optical path. Insertion of the pinhole plate 42p into the optical path during the subjective examination enables a pinhole test to determine whether or not the subject eye E can be corrected with glasses. Note that the pinhole plate 42p is not limited to the configuration illustrated in FIG. 2 as long as it is provided at a position substantially conjugate with the pupil of the subject eye E on the optical path.

The optotype to be displayed on the display 42a for the subjective examination is not particularly limited, provided that the optotype can be used in the eye examination. For example, the optotype includes a Landolt ring, a Snellen chart, an E chart, and the like. The optotype may be a still image or a moving image. The ophthalmologic apparatus 1 including the display 42a, such as an LCD, enables the display of the desired optotype in shape, mode, and contrast at a predetermined examination distance and various types of detailed eye examinations. The ophthalmologic apparatus 1 includes two displays 42a corresponding to the left and right subject eyes E, respectively. Thus, the ophthalmologic apparatus 1 enables the display of the optotype for parallax corresponding to a predetermined examination distance (presentation position) and the simple and precise stereoscopic vision examination with the natural orientation of the visual axis.

Furthermore, the optotype projection system 42 presents the fixation target (optotype) in a predetermined presentation condition to the subject eye E during the fogging to the subject eye E. For example, the "presentation condition" is indicated with the presentation position of the fixation target. In the first embodiment of the presentation condition is indicated with a diopter conversion value based on the presentation position of the fixation target for simplification.

The refraction measurement system 43 is an example of the objective measurement optical system and measures the refractive power of the subject eye E. In the first embodiment, the refraction measurement system 43 has a function to project a predetermined measurement pattern onto the fundus Ef of the subject eye E and a function to detect an image of the measurement pattern projected on the fundus Ef. That is, the refraction measurement system 43 includes a ring-shaped light flux projection system 43A that projects a ring-shaped measurement pattern onto the fundus Ef of the subject eye E and a ring-shaped light flux reception system 43B that receives and/or detects the reflected light of the ring-shaped measurement pattern from the fundus Ef.

The ring-shaped light flux projection system 43A includes a refraction light-source unit 43a, a fourth relay lens 43b, an eye-ring diaphragm 43c, a second field lens 43d, a holed prism 43e, and a rotary prism 43f. The ring-shaped light flux projection system 43A shares the third dichroic filter 42j with the optotype projection system 42 (subjective measurement optical system 44) and shares the first dichroic filter 41b and the objective lens 41a with the observation system 41. The refraction light-source unit 43a includes a refraction-measurement light source 43g for the refraction measurement including, for example, an LED, a collimator lens 43h, a conical prism 43i, and a ring-pattern formation plate 43j. The refraction light-source unit 43a is controlled by the controller 40 to move integrally on the optical axis of the refraction measurement system 43.

The ring-shaped light flux reception system 43B includes a hole 43p of the holed prism 43e, a third field lens 43q, a third reflective mirror 43r, a fifth relay lens 43s, a second focusing lens 43t, and a fourth reflective mirror 43u. The ring-shaped light flux reception system 43B shares the objective lens 41a, the first dichroic filter 41b, the second dichroic filter 41e, the image-forming lens 41f, and the imaging element 41g with the observation system 41. Furthermore, the ring-shaped light flux reception system 43B shares the third dichroic filter 42j with the optotype projection system 42 (subjective measurement optical system 44) and shares the rotary prism 43f and the holed prism 43e with the ring-shaped light flux projection system 43A.

When the refraction measurement system 43 measures the refractive power of the subject eye E, the controller 40 first turns on the refraction-measurement light source 43g. Then, the controller 40 moves the refraction light-source unit 43a of the ring-shaped light flux projection system 43A and the second focusing lens 43t of the ring-shaped light flux reception system 43B in the optical axis direction. Next, in the ring-shaped light flux projection system 43A, the refraction light-source unit 43a emits a ring-shaped measurement pattern. The measurement pattern travels through the fourth relay lens 43b, the eye-ring diaphragm 43c, and the second field lens 43d to the holed prism 43e. Then, the measurement pattern is reflected by a reflective face 43v of the holed prism 43e and guided to the third dichroic filter 42j through the rotary prism 43f. The ring-shaped light flux projection system 43A guides the measurement pattern to the objective lens 41a through the third dichroic filter 42j and the first dichroic filter 41b, so that the ring-shaped measurement pattern is projected on the fundus Ef of the subject eye E.

The ring-shaped light flux reception system 43B condenses the ring-shaped measurement pattern formed on the fundus Ef with the objective lens 41a and then guides the ring-shaped measurement pattern to the hole 43p of the holed prism 43e through the first dichroic filter 41b, the third dichroic filter 42j, and the rotary prism 43f. Next, the ring-shaped light flux reception system 43B guides the measurement pattern through the third field lens 43q, the third reflective mirror 43r, the fifth relay lens 43s, the second focusing lens 43t, the fourth reflective mirror 43u, the second dichroic filter 41e, and the image-forming lens 41f to form the image on the imaging element 41g. Thus, the imaging element 41g detects the image of the ring-shaped measurement pattern, and the controller 40 displays, on the display 31, the image of the measurement pattern detected by the imaging element 41g. Then, the controller 40 measures the spherical power, the cylindrical power, and the axial angle as refractive power based on an image signal from the imaging element 41g.

Note that the configurations of the refraction measurement system 43, the first alignment system 45, the second alignment system 46, and the kerato-measurement system 47, the subjective examination, and the principles of measurement of the refractive power (refraction) of the subject eye and the cornea shape (kerato-shape) of the subject eye are known, and thus the detailed descriptions thereof are omitted.

Next, the procedure of the control processing for the subjective examination for the far-point power (visual acuity test) together with the objective monitoring by the controller 40 will be described with reference to the flowchart illustrated in FIG. 3. The subjective examination starts after the examinee sits in front of the ophthalmologic apparatus 1 and the line of sight of the subject eye E is fixed to the fixation target.

Step S1 corresponds to a step of focusing the subject eye E on the fogging start position. For example, Step S1 is performed in accordance with the following procedure. That is, the controller 40 computes the tentative spherical power S and the cylindrical power C for the subject eye E based on the captured image of the ring image obtained with the refraction measurement system 43. Then, the controller 40 controls the second focusing lens 43t to move the focal position of pattern light to the position corresponding to the spherical equivalent (S+C/2) (position corresponding to tentative far point, namely, fogging start position) based on the computation result of the tentative spherical power S and the cylindrical power C. Note that an "amount of fog" is the amount or intensity of the fog applied to the subject eye E and is represented as the presentation position of the fixation target (presentation distance). The "amount of fog" is also referred to as the "degree of fogging" herein.

Figure 4:
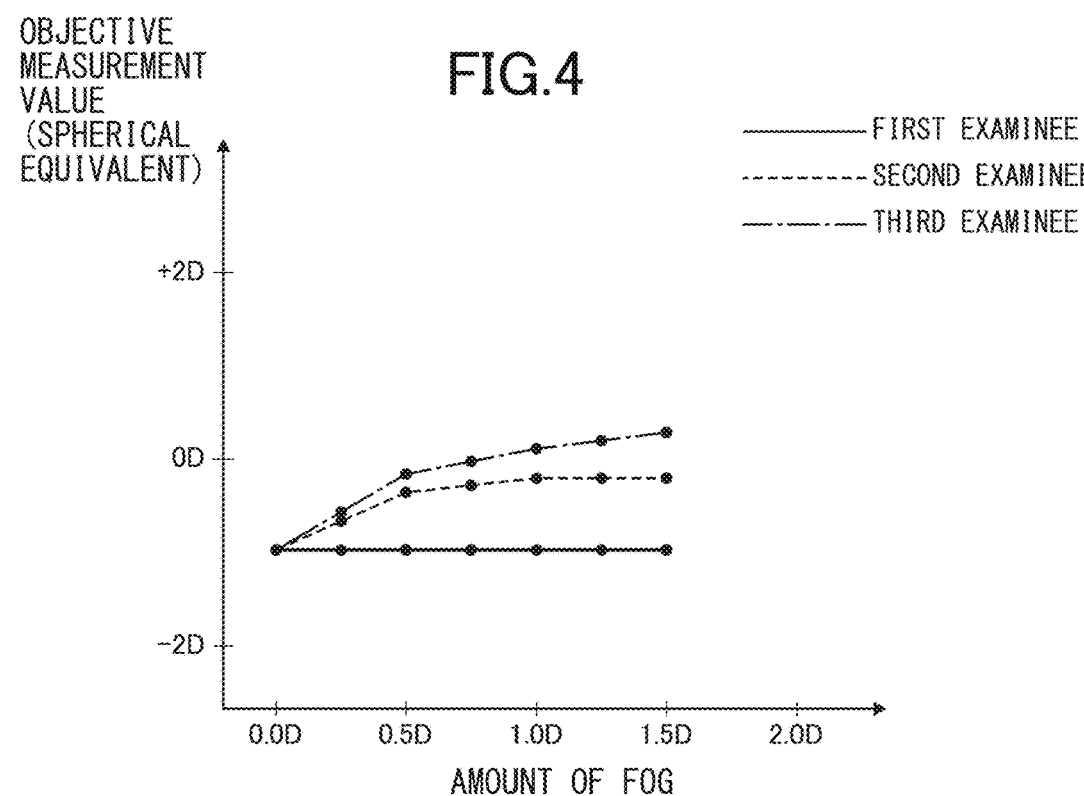
FIG. 4 is a two-dimensional coordinates graph indicating an example of relational characteristics between the objective measurement value (spherical equivalent) and an amount of fog varying in fogging control performed by the controller according to the first embodiment.

After the preliminary measurement in Step S1, the fogging control is performed in Step S2, and then the process proceeds to the next Step S3. Here, the "fogging control" is the control to verify whether the crystalline lens of the subject eye E is relaxed or not before the subjective examination by monitoring the objective measurement value (or spherical equivalent) when the amount of fog gradually is increased to the positive side. For example, as illustrated in FIG. 4, the amount of fog is gradually increased from 0.0D to the positive side at a predetermined degree (e.g., +0.25D) and the objective measurement value is obtained at a time of the gradual increase. Then, characteristic lines, each of which is obtained by connecting, for example, seven points of the objective measurement value to the amount of fog (diopter conversion value), are displayed as a graph. In the case illustrated in FIG. 4, it is determined that the crystalline lenses of the subject eyes E of the second and third examinees may be tense since changes in the objective measurement values are observed. Regarding the first examinee, it is determined that the crystalline lens of the subject eye E is relaxed since no change in the objective measurement value is observed. In a case where the crystalline lens may be tense, the amount of fog is increased until it is determined that the crystalline lens is relaxed. A limit may be set for the amount of increase, and the increase may be stopped according to the set limit even when the lens is tensed. In this case, an alert is issued to indicate that the crystalline lens may be tense. When increasing the amount of fog, the presentation position of the fixation target is moved in the direction of the far vision (positive side). When decreasing the amount of fog, the presentation position of the fixation target is moved in the direction of near vision (negative side). The "Diopter Conversion Value (=D)" is a unit for the refractive power obtained from the reciprocal of the metric distance at which a lens is in focus.

After the fogging control in Step S2, the process proceeds to the "main measurement" in Step S3. The "main measurement" is a step of measuring predetermined eye characteristics. For example, for the objective refraction measurement (refraction measurement), the "main measurement" is performed as follows. That is, the controller 40 controls the ring-shaped light flux projection system 43A to project the ring-shaped measurement pattern onto the fundus Ef of the subject eye E in fogging. Then, the controller 40 controls the ring-shaped light flux reception system 43B to receive and/or detect the reflected light of the ring-shaped measurement pattern from the fundus Ef and measures the spherical power, the cylindrical power, and the cylindrical-axis angle as the refractive power based on the image signal from the imaging element 41g. Note that the processes in Steps S1 to S3 correspond to the objective examination process and the processes from Step S4 correspond to the subjective examination process including the RG test, the weakest power test, and the like. The subjective examination process starts after it is verified that the crystalline lens of the subject eye E is relaxed. The subjective examination process is performed for each of the eyes from the start till the binocular balance test.

After it is determined that the main measurement in Step S3 has been completed or after a change of the subject eye E in Step S12, the subjective examination is set to start for the right eye or the left eye in Step S4. Then, the process proceeds to Step S5. Here, the "subjective examination is set to start" corresponds, for example, to setting, to the phoropter built in the ophthalmologic apparatus 1, the value obtained from the addition of +0.50D to the spherical power for fogging based on the spherical equivalent (e.g., −1.0D) obtained in the main measurement.

Figure 5:
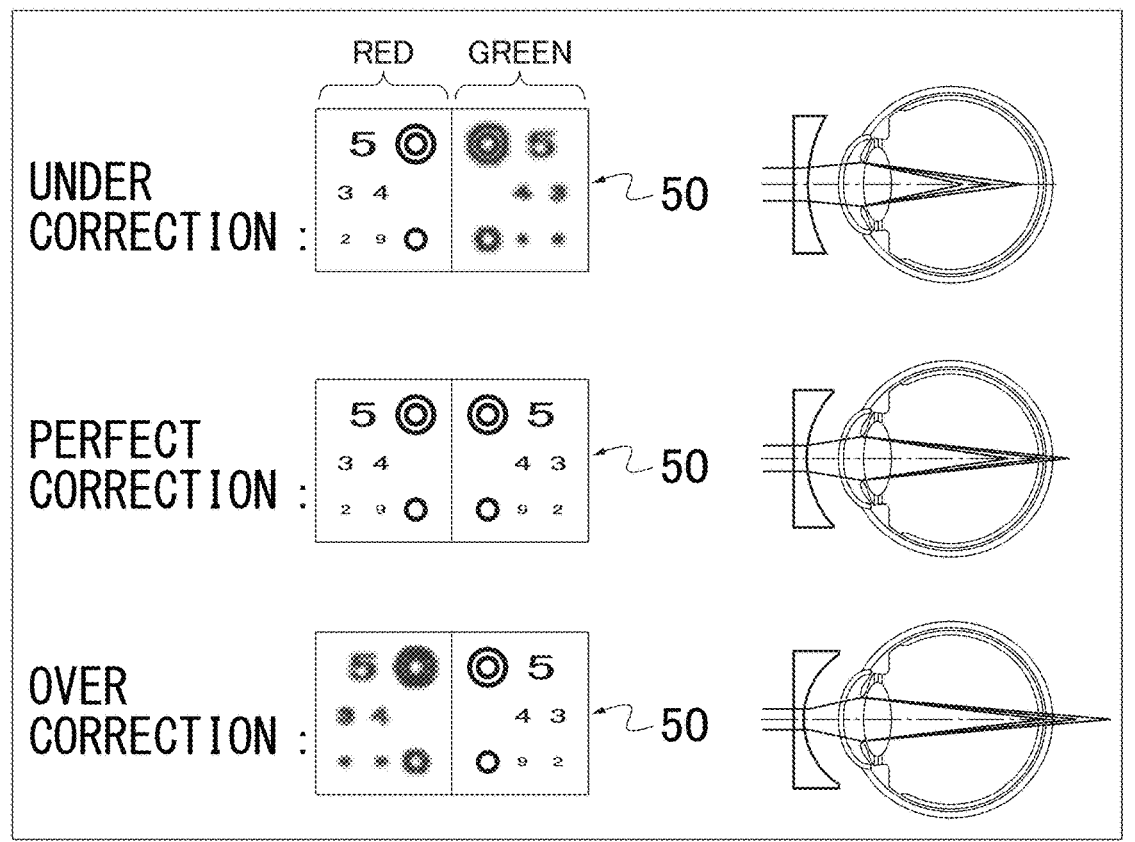
FIG. 5 is an explanatory view of an RG test for undercorrection, perfect correction, and overcorrection carried out by the controller according to the first embodiment.

After the subjective examination is set to start in Step S4, the RG test is carried out with an RG chart 50 in Step S5. Then, the process proceeds to Step S6. FIG. 5 illustrates the "RG chart 50". The "RG chart 50" illustrated in FIG. 5 includes, for example, red icons and green icons arranged laterally. The red icons include, as the optotypes, numbers different in size and a double circular mark, and a single circular mark different in size. Also, the green icons include, as the optotypes, numbers different in size and a double circular mark and a single circular mark different in size. The "RG test" is a test using the RG chart 50 to check whether the corrected power is overcorrected or undercorrected based on the optical characteristic called chromatic aberration. Due to the characteristics of the translucent body of the eye, the shorter the wavelength of light, the greater the power on the refractive surface. Thus, the green wavelength of light forms an image at a position closer to the incident side than the red wavelength of light. Therefore, in the case illustrated on the upper side in FIG. 5 in which the subject eye E is undercorrected (in undercorrection), the optotype is formed ahead of the retina while the red wavelength of light forms an image closer to the retina (rear side). Accordingly, the red optotype can be seen more clearly. In the state illustrated in the middle in FIG. 5 in which the subject eye E is perfectly corrected, the green and red optotypes can be seen as substantially equivalent. In the state illustrated at the bottom of FIG. 5, in which the subject eye E is overcorrected (in overcorrection), the green optotype can be seen more clearly. Therefore, in the RG test, accommodation or adjustment is made by adding or changing corrective lenses such that the green and red optotypes on the RG chart 50 can be seen as equivalent.

After the RG test in Step S5, the adjustments of the cylindrical axis (astigmatic axis), the cylindrical power (astigmatic power), and the spherical power are performed in Step S6. Then, the process proceeds to Step S7. Here, the "adjustments of the cylindrical axis, the cylindrical power, and the spherical power" are performed by selecting the cross-cylinder-test optotype icon from the chart page and by rotating the variable cross-cylinder lens 42h such that the test optotype can be clearly seen. Therefore, the "adjustments in the cylindrical axis, the cylindrical power, and the spherical power" are also referred to as a cross-cylinder test. As the cross-cylinder-test optotype icon, for example, an icon including many dots gathered in a circular shape is used.

Figure 6:
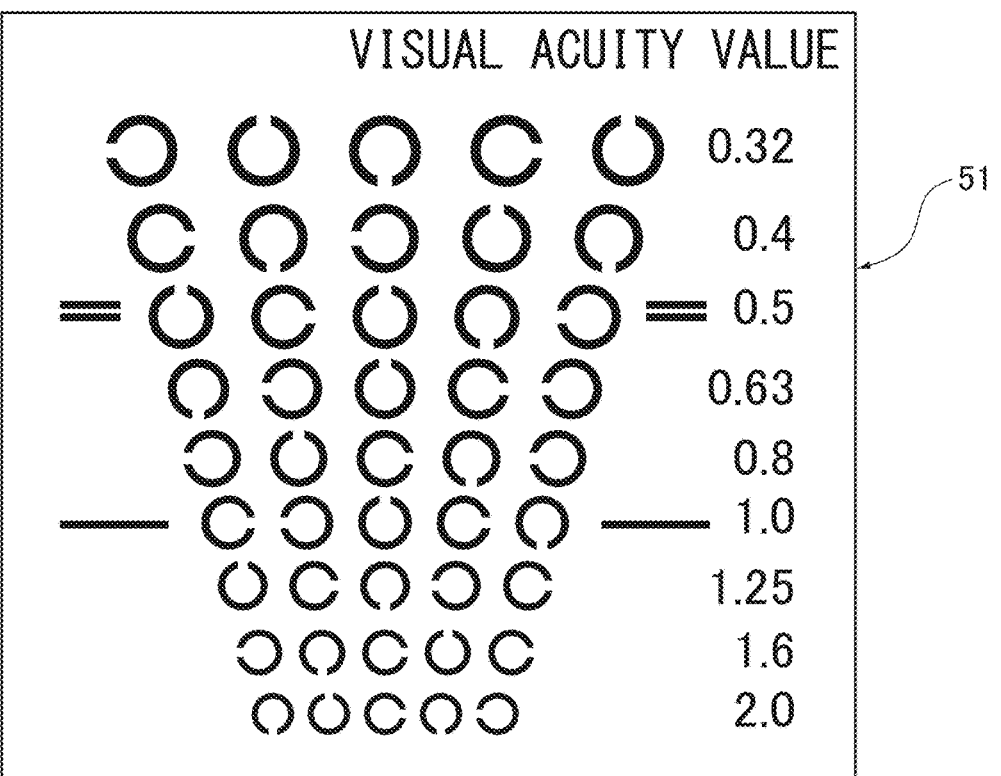
FIG. 6 illustrates an exemplary decimal-point visual-acuity value optotype or eye chart used as an ETDRS chart in the weakest power test to be carried out by the controller according to the first embodiment.
Figure 7:
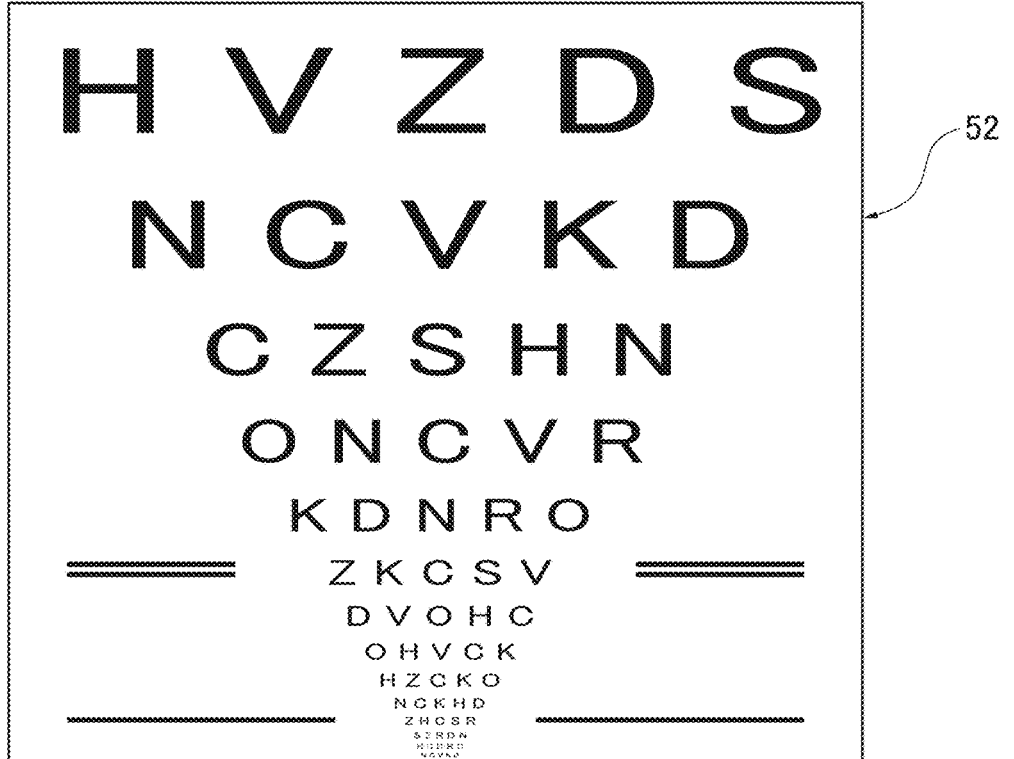
FIG. 7 illustrates an exemplary fractional visual-acuity value optotype or eye chart used as an ETDRS chart in the weakest power test to be carried out by the controller according to the first embodiment.

After the adjustments in the cylindrical axis, the cylindrical power, and the spherical power in Step S6 or the change to the internal lens in Step S9, the measurement of a LogMAR visual acuity value is performed using an ETDRS chart in Step S7. Then, the process proceeds to Step S8. ETDRS stands for "Early Treatment Diabetic Retinopathy Study", and LogMAR stands for "Logarithm of the Minimum Angle of Resolution". As the ETDRS chart, for example, a decimal-point visual-acuity value optotype 51 illustrated in FIG. 6 or a fractional visual-acuity value optotype 52 illustrated in FIG. 7 is used. The "measurement of a LogMAR visual acuity value" corresponds to the measurement of the visual acuity value using the ETDRS chart in which the Landolt rings or the letters of the alphabet (also collectively referred to as optotype marks) are arranged in a geometric progression manner as illustrated in FIGS. 6 and 7. When the optotype marks are the geometric progression, the logarithms have equal intervals, which is convenient for statistical processing such as the averages and standard deviations. The decimal-point visual-acuity value optotype 51 illustrated in FIG. 6 is typically used in Japan while the fractional visual-acuity value optotype 52 illustrated in FIG. 7 is typically used overseas. The above optotypes are only examples, and any optotype for the visual acuity measurement may be used for the measurement of the visual acuity value. Then, the LogMAR visual acuity value measured in Step S7 is regarded as the maximum visual acuity value based on the visual acuity test at that time.

After the measurement of the LogMAR visual acuity value in Step S7, it is determined whether or not the visual acuity value has converged to the target value in Step S8. If the determination result is YES, the process proceeds to Step S10. On the other hand, if the determination result is NO, the process proceeds to Step S9. The "target value" is not limited to a target value, which is the maximum visual acuity value, for the visual acuity value in a test for the weakest power that provides the highest visual acuity value and may be a target value, which is an intended visual acuity value, for the visual acuity value in a test for the weakest power enabling the recognition of an optotype at a set intended visual acuity value.

After it is determined that the maximum visual acuity value has not converged to the target value in Step S8, the internal lenses of the ophthalmologic apparatus 1 are changed in Step S9. Then, the process returns to Step S7. The process is repeated until it is determined that the visual acuity value has converged to the target value by the subjective examination. Here, changing the internal lenses of the ophthalmologic apparatus 1 means, for example, automatically or manually switching or replacing the corrective lenses that change the spherical power by, for example, +0.25D.

After it is determined that the visual acuity value has converged to the target value in Step S8, the weakest power enabling the recognition at the maximum visual acuity value or an intended visual acuity value is obtained and then the obtained weakest power is set as the subjective refractive value in the subjective examination in the ophthalmologic apparatus 1 in Step S10. Then, the process proceeds to Step S11.

After the setting of the subjective refractive value in Step S10, it is determined whether or not the left and right eyes have been examined in Step S11. If the determination result is YES, the process proceeds to Step S13. On the other hand, if the determination result is NO, the process proceeds to Step S12.

After it is determined that the left eye or the right eye has not been examined in Step S11, the subject eye E is changed in Step S12. Then, the process returns to Step S4. For example, in a case where the right eye has already been examined as the subject eye E, the subject eye E is changed to the left eye that has not been examined yet. After the subject eye E is changed to the other subject eye E, the RG test and the weakest power test are performed on the other subject eye E until it is determined that the left and right eyes have been both examined.

Figure 8:
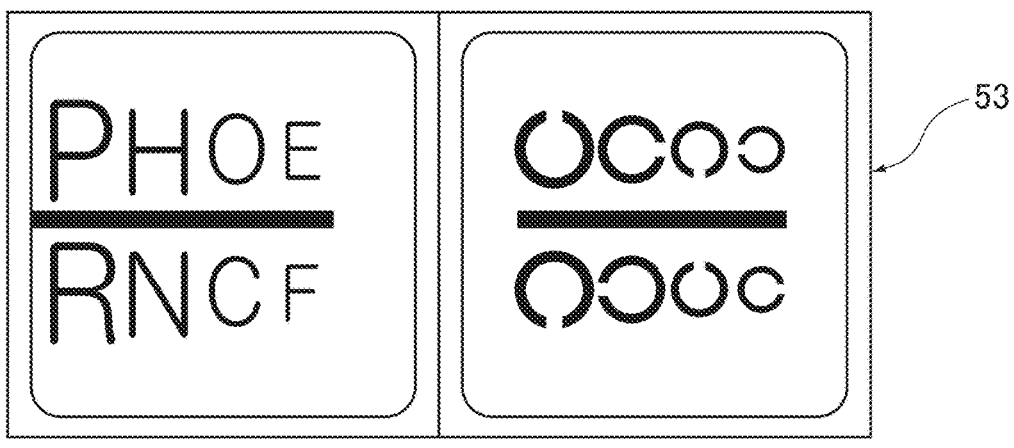
FIG. 8 illustrates an exemplary binocular-balance-test optotype icon used in a binocular balance test to be carried out by the controller according to the first embodiment.

After it is determined that the left and right eyes have been examined in Step S11, the binocular balance test is performed to adjust the balance between the left vision and the right vision in Step S13. Then, the process proceeds to Step S14. In the binocular balance test, a binocular-balance-test optotype icon 53 illustrated in FIG. 8 is selected from the chart page. For example, the binocular-balance-test optotype icon 53 includes, as optotypes, the letters of the alphabet and Landolt rings different in size. The letters are divided into two groups and the first group is arranged on the upper side while the second group is arranged on the bottom side as illustrated in FIG. 8. Similarly, the Landolt rings are divided into two groups, and the first group is arranged on the upper side while the second group is arranged on the bottom side. The examinee is asked to look at the upper side with the right eye and the lower side with the left eye (optotypes corresponding to left and right eyes can be presented with internal optotypes in the apparatus). Then, the examinee is asked to indicate which side he or she sees better by comparing how the letters or rings on the upper side are seen with the right eye to how the letters or rings on the lower side are seen with the left eye. Then, when the ways in which the letters or rings are seen on the upper and lower sides are the same, the examination is finished. Alternatively, if the eye (e.g., right eye) that can see the letters or rings better is changed to the other eye (e.g., left eye) between the previous result and the current result, the examination is finished in the state with the previous result. When the binocular balance test is performed with the optotypes viewed simultaneously with both eyes as the subject eye E and it is determined that the binocular balance is vague, a cause for the vagueness is verified by the monocular examination of the subject eye E with the monocular occlusion or by the monocular examination of the subject eye E with the binocular opening. When performing the monocular examination of the subject eye E with the monocular occlusion or the monocular examination of the subject eye E with the binocular opening, binocular-balance-test optotype icons with two deflection colors are selected, for example.

After the binocular balance test in Step S13, the subjective refractive values and the maximum visual acuity values of both eyes as the measurement results by the examination in the above process are recorded in Step S14. Then, the process proceeds to the end.

In Step S15, the refraction measurement is performed to obtain refractive values on a time series basis in real-time, simultaneously with the subjective examination including the RG test and the weakest power test between the start and end of the subjective examination. This is because the controller 40 of the ophthalmologic apparatus 1 is characterized in that it performs the refraction measurement of the subject eye E by the refraction measurement system 43, which is the objective measurement optical system, and performs the objective monitoring to monitor the refractive values as the objective measurement information during the subjective examination by the subjective measurement optical system 44.

In Step S16, a command for displaying the objective measurement information is output to the examiner controller 30 at predetermined timing including time intervals. The objective measurement information to be displayed is, for example, information with a two-dimensional coordinates graph that indicates the relationship between the objective measurement values (spherical equivalent calculated from the refractive values) and the power of the corrective lens for the subject eye E or time from the start of the subjective examination (see two-dimensional coordinates graphs G, G', and G" in FIGS. 9, 10, and 11). For example, the "predetermined timing" may be the timing at which the spherical power is changed by the corrective lens in Step S9 or the timing at which a voice of the examinee who reads the optotype is recognized. Alternatively, the information may be displayed in real-time each time measurement is performed. The values to be displayed may be the mean or average of the values obtained during the time interval for displaying.

In Step S17, the refractive values are monitored at least from the start of the RG test with the RG chart 50 in Step S5 to the end of the RG test, and a comparison is performed to check if there is any difference or variation in the refractive values. Then, it is determined that an accommodation intervention by the subject eye E has occurred in the RG test if the refractive value is found based on the comparison result to have a difference equal to or greater than a threshold or a fluctuation equal to or greater than a threshold. Then, an alert is issued or feedback is given to the eye examination contents. The feedback corresponds to taking a measure to reduce the accommodation intervention, such as changing the spherical power of the corrective lens by −0.25D or asking the examinee to look far away.

Next, the effect of the RG test with the RG chart 50 by the ophthalmologic apparatus 1 will be described with reference to FIGS. 3, 5, and 9 to 13.

According to conventional technology, there are no means for determining the accommodation intervention by the subject eye at the time of the RG test for checking whether or not the corrected power is overcorrected or undercorrected by the subjective measurement optical system. According to this conventional technology, it is assumed that the adjustment function of focusing by the crystalline lens of the subject eye is relaxed by introducing the fogging method into the subjective examination. At the stage of the RG test in the subjective examination for the far-point power, the examinee is asked to answer how he or she sees the RG chart, thereby checking whether the corrected power is undercorrected, perfectly corrected, or overcorrected (in underreaction, perfectly correction, or overcorrection) (see FIG. 5).

However, during the RG test, the accommodation function of the subject eye is likely to intervene, for example, in a case where the subject eye has difficulty in doing fixation due to the examination fatigue or in a case where the subject eye keeps gazing at the red icons of the RG chart. Therefore, direct use of the test result from the RG test, in which the accommodation intervention by the subject eye has occurred, causes a deterioration in the accuracy of checking the corrected power based on the RG test. According to the conventional technology, there are no means for determining the accommodation intervention by the subject eye at the time of the subjective examination. Thus, it is difficult to determine or verify whether or not the accommodation intervention by the subject eye has occurred in the RG test.

For a demand for determination of the accommodation intervention by the subject eye during the RG test, the inventors of the present disclosure have noticed that the variation of the objective measurement values (spherical equivalent) can be inhibited if the ciliary muscle of the crystalline lens does not react to the gaze of the red target or the like and the subject eye E is relaxed. On the other hand, the inventors focused on the objective measurement values (spherical equivalent) vary if the intervention of the accommodation by the subject eye E in which the ciliary muscle of the crystalline lens reacts to the gaze of the red target or the like occurs. Based on the above points, the controller 40 measures the objective refractive characteristics of the subject eye E with the objective measurement optical system (refraction measurement system 43) during the RG test for checking whether or not the corrected power is overcorrected or undercorrected by the subjective measurement optical system 44. Along with the objective measurement, the objective monitoring is performed to monitor the objective measurement information obtained by the measurement of the objective refractive characteristic.

The effect of the RG test will be described below with reference to the two-dimensional coordinates graph G as a first monitoring display example indicating the relationship between the objective measurement values (spherical equivalent) and the power of the corrective lens illustrated in FIG. 9. First, at the start of the RG test, when the process proceeds in the order of S1, S2, S3, and S4 in the flowchart of FIG. 3 and the subjective examination is set to start in Step S4, an initial refractive value in which, for example, the power of the corrective lens is −0.50D and the objective measurement value (spherical equivalent) is −1.0D, is set.

Figure 3:
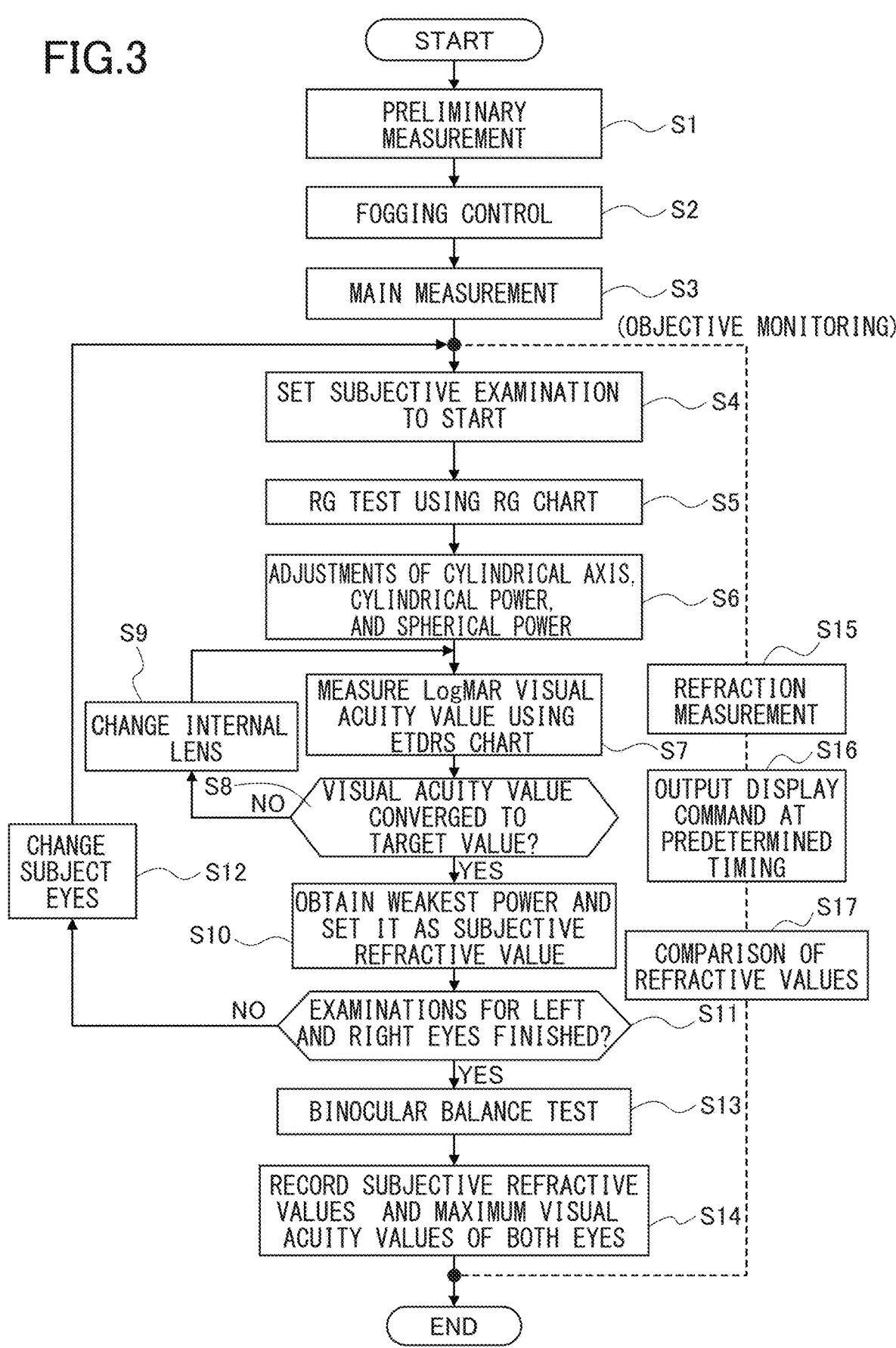
FIG. 3 is a flowchart of a procedure of control processing for the subjective examination of far-point power (visual acuity test) together with objective monitoring to be performed by a controller according to the first embodiment.

Then, the adjustment is performed by adding or replacing the corrective lens in the RG test from S4 to S5 in the flowchart of FIG. 3 until the green and red optotypes are seen to be equivalent in the RG chart 50. Then, the process proceeds in the order of S6, S7, S8, and S9. At the time of the change to the internal lens in Step S9, the power of the corrective lens is changed from −0.50D determined in the RG test in Step S5 to −0.75D. Then, the first objective monitoring is performed and a first refractive value is set. Then, the process proceeds from S9 through S7 and S8 to S9 in the flowchart of FIG. 3. At the timing of the change to the internal lens in Step S9, the power of the corrective lens is changed from −0.75D to −1.00D. Then, the second objective monitoring is performed and a second refractive value is set. Further, the process proceeds from S9 through S7 and S8 to S9 in the flowchart of FIG. 3. At the timing of the change to the internal lens in Step S9, the power of the corrective lens is changed from −1.00D to −1.25D. Then, the third objective monitoring is performed and a third refractive value is set.

As described above, the powers of the corrective lens are changed in steps of −0.25D (changes in negative side in power in FIG. 9), and the refractive values as the measurement results due to the refraction measurement are connected to produce the refractive-value characteristic graph. At this time, in a case where the accommodation intervention of the subject eye E has not occurred from the start to the end of the RG test, the refractive-value characteristic graph having the initial refractive value, the first refractive value, the second refractive value, and the third refractive value at −1.0D is produced in the two-dimensional coordinates graph G illustrated in FIG. 9. On the other hand, assume that when the power of the corrective lens is changed from −0.75D to −1.00D, for example, the accommodation intervention of the subject eye E occurs by gazing at the red side and the accommodation intervention is maintained. In this case, in the two-dimensional coordinates graph G illustrated in FIG. 9, a refractive-value characteristic graph having a lower second refractive value and a lower third refractive value is produced. The lower second refractive value is shown with a filled circle (black circle) and is lower than the second refractive value shown with an open circle (white circle) with no accommodation intervention of the subject eye E. The lower third refractive value is shown with a filled circle (black circle) and is lower than the third refractive value shown with an open circle (white circle). In the produced refractive-value characteristic graph, the lower second refractive value and the lower third refractive value are lower than the initial refractive value of −1.0D as illustrated in FIG. 9. In such a case, in Step S17, it is determined that the accommodation intervention by the subject eye E has occurred and an alert is issued or feedback is given to the eye examination contents. This makes it possible to proceed to the next step of the subjective measurement while preventing the accommodation intervention of the subject eye E during the RG test.

As described above, in a case where the refractive-value characteristic graph is produced by connecting the refractive values as the measurement results by the refraction measurement between the start and the end of the RG test, and the graph indicates the graph characteristics with no variation in the refractive values, it is possible to determine or verify that there is no accommodation intervention of the subject eye E only by viewing the two-dimensional coordinates graph G. Also, in a case where the graph indicates the graph characteristics with variation in the refractive values, it is possible to determine or verify that there is the accommodation intervention of the subject eye E only by viewing the two-dimensional coordinates graph G.

Figure 10:
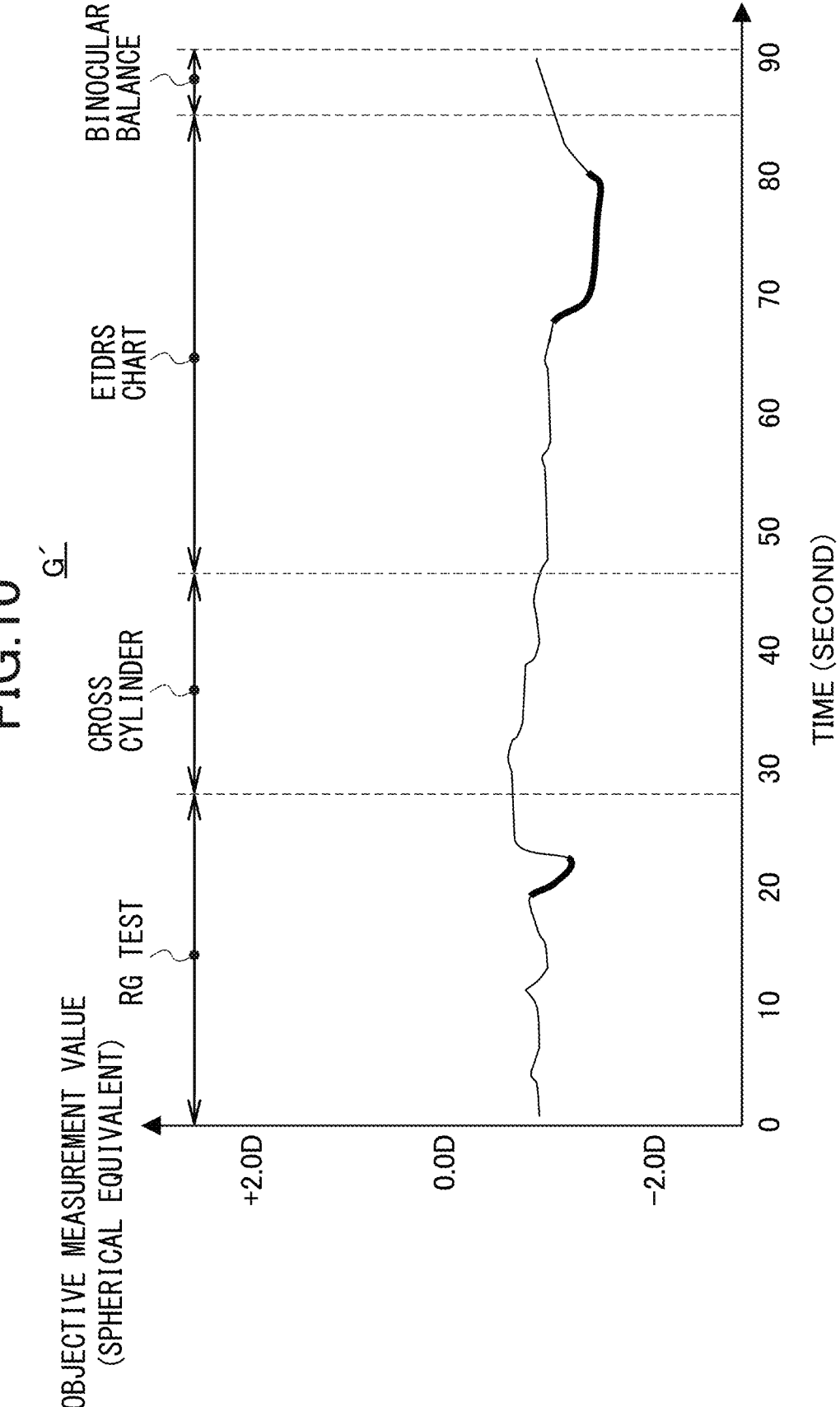
FIG. 10 is a two-dimensional coordinates graph as a second monitoring display example based on the relationship between the objective measurement value (spherical equivalent) and time from the start of the examination in the subjective examination.

As another embodiment of the two-dimensional coordinates graph G, FIG. 10 illustrates a two-dimensional coordinates graph G' as a second monitoring display example. Referring to FIG. 10, the horizontal axis represents the time from the start of the subjective examination, instead of the power of the corrective lens. With the transition in the order of the RG test, the cross-cylinder test, the ETDRS chart, and the binocular balance with the elapse of time, the objective measurement values (spherical equivalent) are plotted. In this case, an alert is issued at points where the objective measurement values (spherical equivalent) change or vary relatively large as shown by thick solid lines in FIG. 10. The two-dimensional coordinates graph G' may show the RG test, the cross-cylinder test, the ETDRS chart, and the binocular balance by color coding for easy understanding of the examination content in time.

Figure 11:
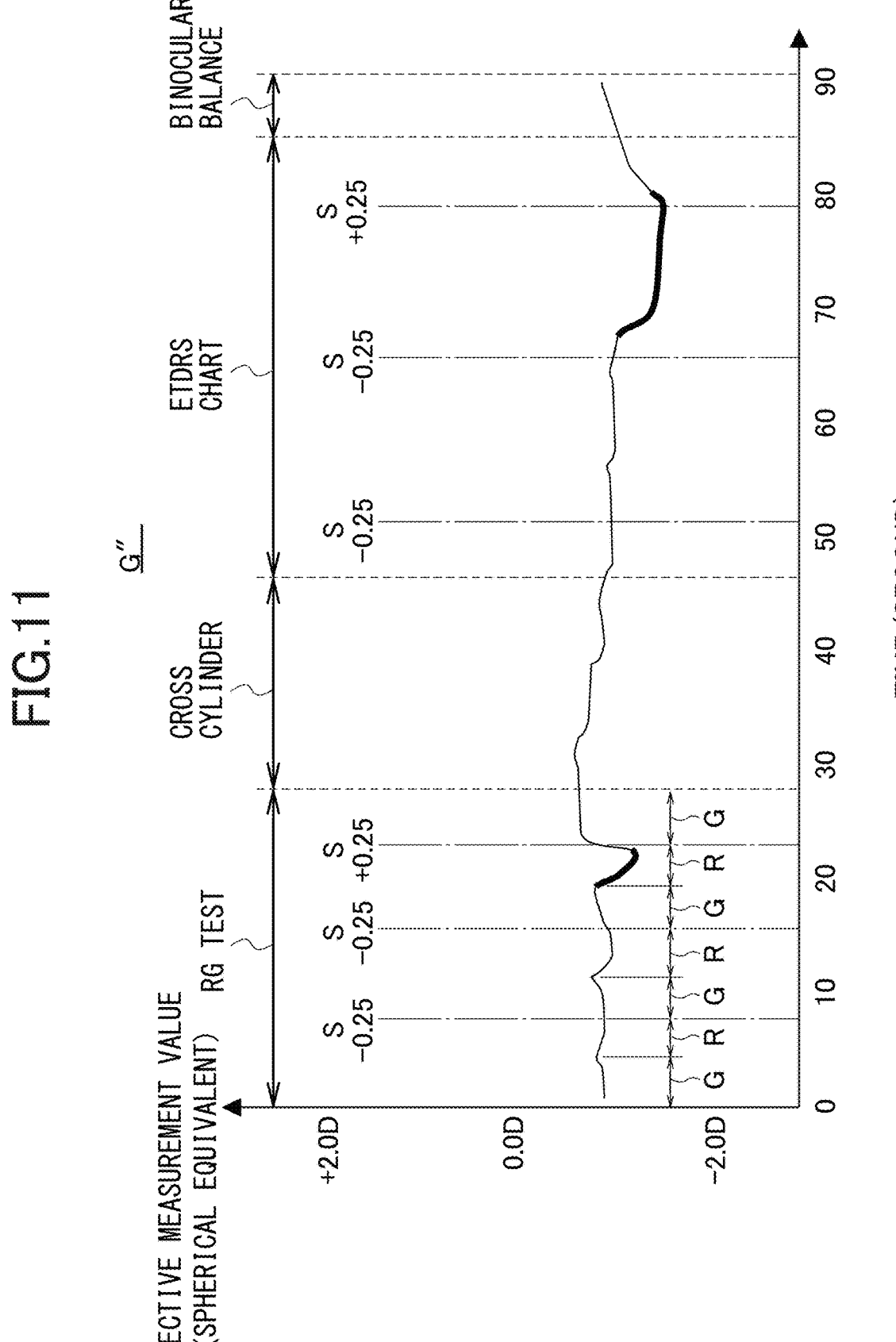
FIG. 11 is a two-dimensional coordinates graph as a third monitoring display example based on the relationship between the objective measurement value (spherical equivalent), time from the start of the examination in the subjective examination, and an additional lens.

FIG. 11 illustrates a two-dimensional coordinates graph G" as a third monitoring display example. Referring to FIG. 11, similar to FIG. 10, the horizontal axis represents the time from the start of the subjective examination. With the transition in the order of the RG test, the cross-cylinder test, the ETDRS chart, and the binocular balance with the elapse of time, the objective measurement values (spherical equivalent) are plotted. In this case, the graph shows, in the RG test and the ETDRS chart, the spherical power S (cylindrical power C may also be indicated) at the time of the lens change. In the RG test, the analysis is performed to determine which of the R and G optotypes the subject eye E is looking at based on the direction of the line of sight and the graph shows the analysis result. Also, the graph may show the spherical power S, the cylindrical power C, the cylindrical-axis angle A, or the spherical equivalent (SE) at the point in time when the spherical power S of the lens is changed. Similar to the example in FIG. 10, an alert may be issued at points where the objective measurement values (spherical equivalent) change or vary relatively large as shown by the thick solid lines in FIG. 11. Alternatively, an alert may be issued when there are minor variations.

Figure 12:
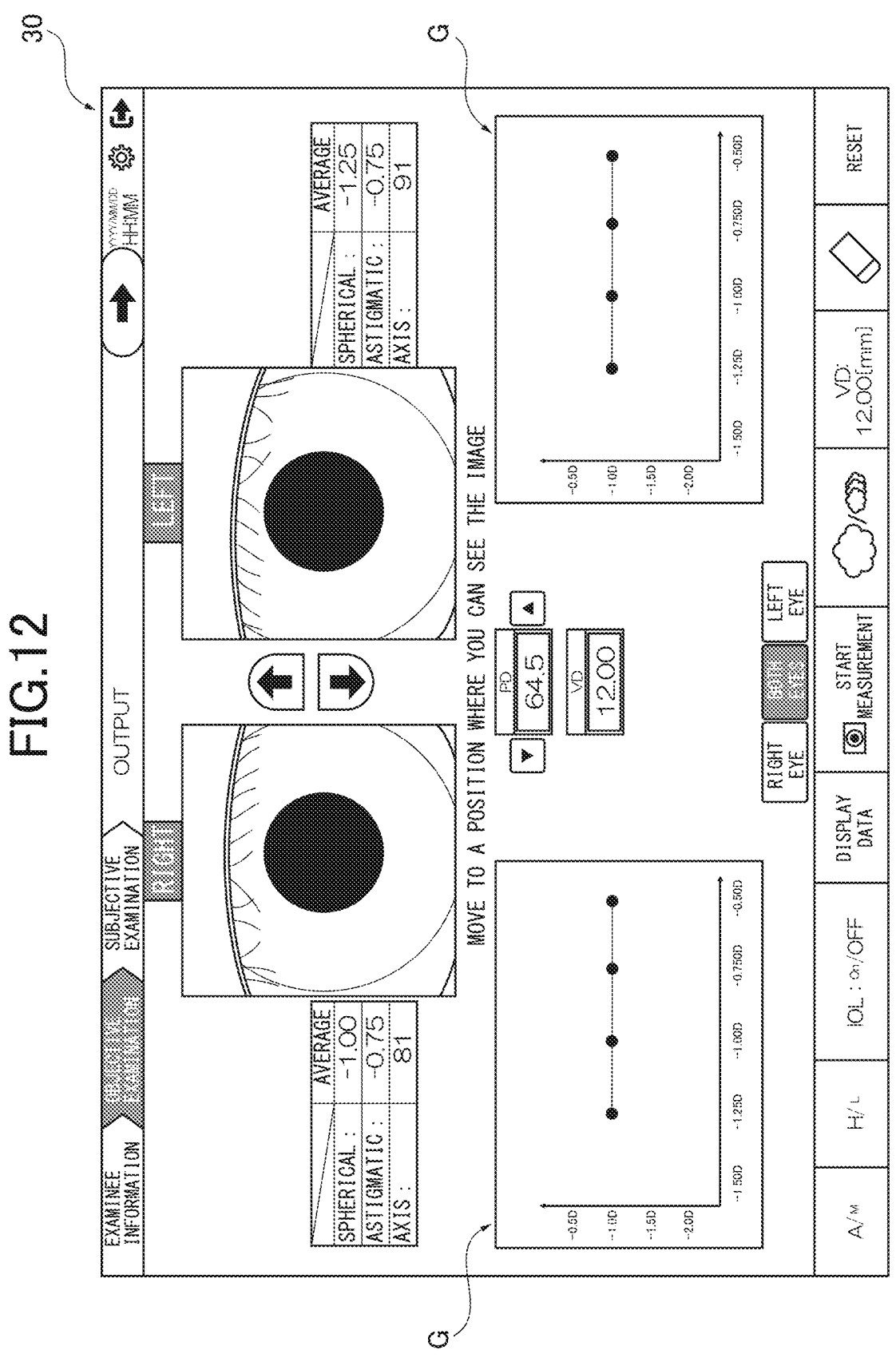
FIG. 12 illustrates an exemplary objective monitoring screen displaying the two-dimensional coordinates graph of FIG. 9 on a display of an examiner controller.

The objective monitoring screen including any one of the two-dimensional coordinates graphs G, G', or G" is a screen as illustrated in FIG. 12, for example. The screen illustrated in FIG. 12 includes the objective measurement screen for both eyes (binocular-simultaneous objective measurement screen) displayed on the display 31 of the examiner controller 30, and the two-dimensional coordinates graphs G of FIG. 9 which are displayed for each of the left and right eyes and superimposed on the objective measurement screen. Note that the objective monitoring screen may be, for example, a screen in which any one of the two-dimensional coordinates graphs G, G', and G" illustrated in FIGS. 9 to 11 is superimposed on the subjective examination screen or is displayed in a pop-up manner on the subjective examination screen. The objective monitoring screen may be, for example, a screen in which the two-dimensional coordinates graph G illustrated in FIG. 9 is displayed independently of the subjective examination screen and/or the objective measurement screen.

Figure 13:
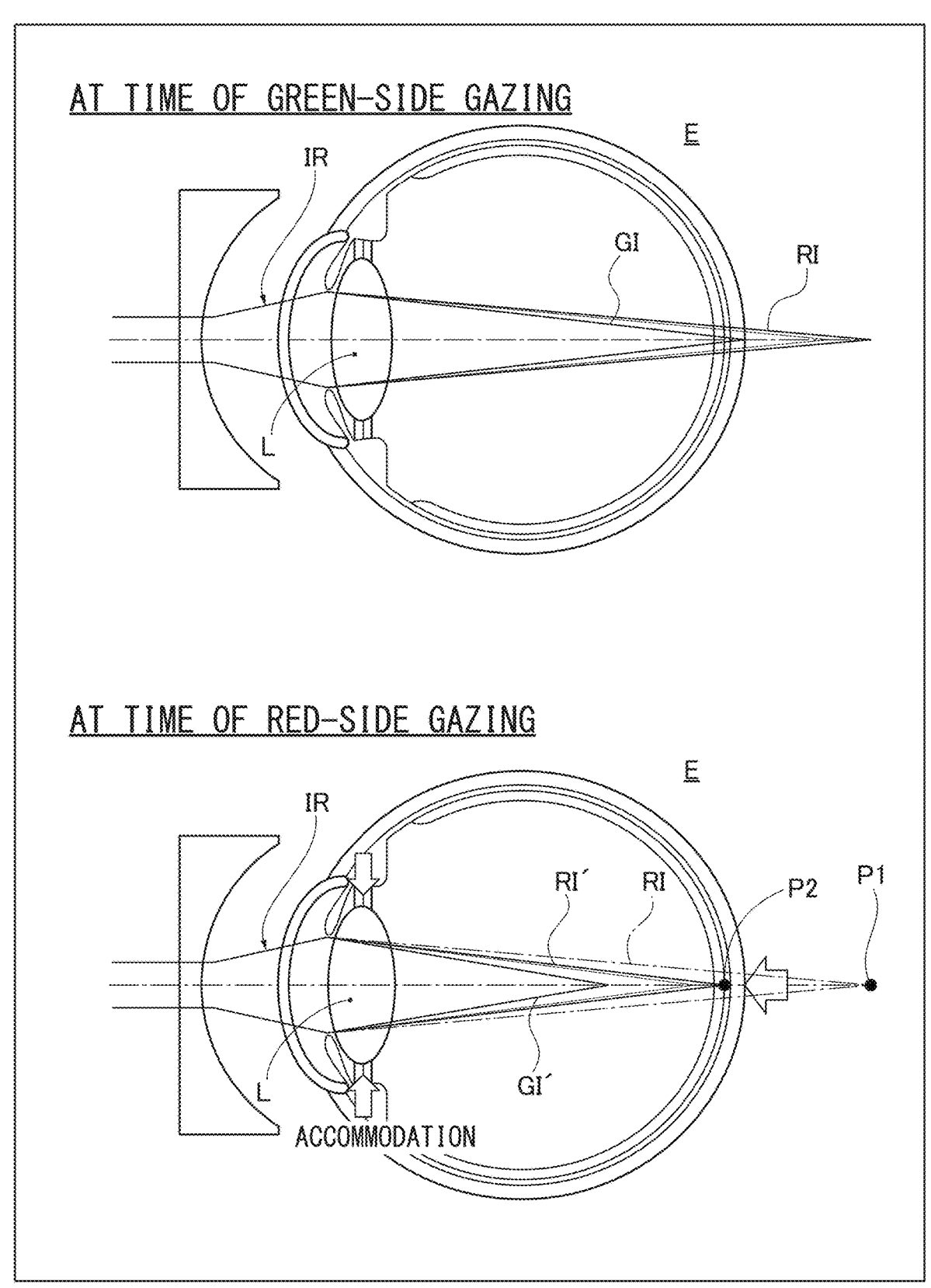
FIG. 13 is an explanatory view for a cause of the intervention of the accommodation function of a subject eye that gazes at the red optotype of the RG chart.

Here, the red-side gazing, which is a particular cause of the accommodation intervention by the subject eye E in the RG test, will be described with reference to FIG. 13. First, when an examination beam IR enters the crystalline lens L and passes through the crystalline lens L, the examination beam IR is divided into a green wavelength component GI and a red wavelength component RI due to the chromatic aberration. In the green optotype gazing at the RG chart 50 with the overcorrection (see bottom side in FIG. 5), the position at which the green wavelength component GI having passed through the crystalline lens L forms an image is close to the retina as illustrated on the upper side in FIG. 13, resulting in being in focus with little or no accommodation or adjustment. On the other hand, in the red optotype gazing at the RG chart 50 with the overcorrection (see bottom side in FIG. 5), the position at which the red wavelength component RI having passed through the crystalline lens L forms an image is behind the retina as illustrated on the bottom side in FIG. 13. When the position at which the red wavelength component RI forms the image is behind the retina, the ciliary muscle of the crystalline lens L of the subject eye E reacts so that the position at which the image is formed is shifted due to the accommodation intervention. Specifically, as shown at the bottom of FIG. 13, the position at which the image is formed is shifted forward from an imaging position P1 at the intersection of the red wavelength components RI shown with dashed-dotted lines to an imaging position P2 at the intersection of the red wavelength components RI' shown with solid lines.

Therefore, gazing at the red optotype makes it easier for the ciliary muscle of the crystalline lens L of the subject eye E to react and cause the accommodation intervention, and continuously gazing at the red optotype increases the probability of the accommodation intervention. The accommodation intervention of the subject eye E may cause a false check result indicating the undercorrection (illustrated on the upper side of FIG. 5) even in the state of the overcorrection (illustrated on the bottom side of FIG. 5). With the undercorrection, the red optotype is in focus, but the green optotype is blurred while with the overcorrection, the green optotype is in focus, but the red optotype is blurred.

Figure 9:
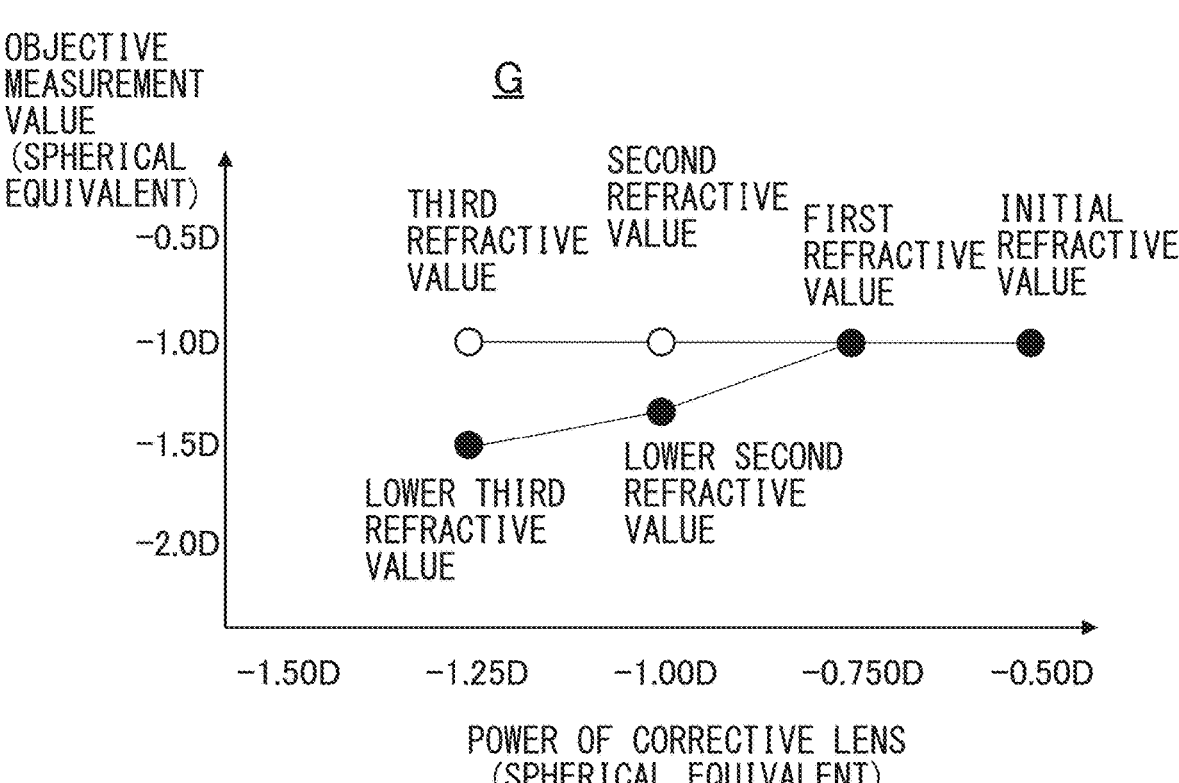
FIG. 9 is a two-dimensional coordinates graph as a first monitoring display example based on the relationship between the objective measurement value (spherical equivalent) and the power of a corrective lens in the RG test.

As described above, at the time of the RG test, displaying the objective measurement information obtained by measuring the objective refractive characteristics (e.g., any of the two-dimensional coordinates graphs G, G', and G" as illustrated in FIGS. 9 to 11) allows the examiner to determine whether or not the accommodation intervention of the subject eye E has occurred by checking the displayed objective monitoring screen. Also, this does not require any measure against the red-side gazing at the time of the RG test. Such a measure includes, for example, the detection of whether or not the subject eye E is in gazing at the red optotype and the determination of whether or not the duration of gazing at the red optotype is above the threshold for determining the accommodation intervention. Furthermore, the determination of the accommodation intervention by the subject eye E can be a measure against the accommodation intervention resulting from causes other than the red optotype gazing. In the embodiment, the alert is issued based on the change or variation in the spherical equivalent. However, the alert may be issued based on a variation in the spherical power, the cylindrical power, or the cylindrical-axis angle at a large degree of the cylindrical power.

As described above, the ophthalmologic apparatus 1 has the following effects.

(1) The ophthalmologic apparatus 1 includes the subjective measurement optical system 44 configured to measure the subjective refractive value of the subject eye E, the objective measurement optical system (refraction measurement system 43) configured to measure the objective refractive characteristics of the subject eye E, and the controller 40 configured to control the subjective measurement optical system 44 and the objective measurement optical system. The controller 40 is further configured to perform the measurement of the objective refractive characteristics of the subject eye E by the objective measurement optical system and perform the objective monitoring to monitor objective measurement information (spherical equivalent) obtained by the measurement of the objective refractive characteristics during the RG test for checking whether or not the corrected power is overcorrected (or in overcorrection) or undercorrected (or in undercorrection) by the subjective measurement optical system 44. Thus, it can be determined whether or not the accommodation intervention by the subject eye E has occurred during the RG test.

(2) The ophthalmologic apparatus 1 is an objective measuring machine that has a subjective function and includes the subjective measurement optical system 44 and the objective measurement optical system (refraction measurement system 43). The objective measurement optical system has a function of simultaneously measuring the objective refractive characteristics of both eyes as the subject eyes E. Thus, the fogging control, the binocular balance test, and the like can be carried out promptly in a short time during the subjective examination.

(3) The controller 40 is configured to monitor the objective measurement values (spherical equivalent) at least from the start to the end of the RG test and to issue an alert or give feedback to eye examination content based on a result of comparison regarding a difference or variation in the objective measurement values. Thus, the examiner can be notified of the accommodation intervention by the subject eye E during the RG test. In addition, the accuracy of the RG test can be improved by eliminating the check result when the accommodation intervention occurs.

(4) The subjective measurement optical system 44 is provided with the RG chart 50 including the red optotype and the green optotype arranged as an optotype for use in the RG test. In the subjective measurement optical system 44, the RG chart 50 including the red optotype and the green optotype arranged together is used as the optotype in the RG test. The controller 40 is configured to check whether or not the corrected power for the subject eye E is overcorrected or undercorrected using the RG chart 50. Thus, it is possible to accurately check whether or not the corrected power is overcorrected or undercorrected by using the RG chart 50 with the red optotype and the green optotype arranged together during the RG test.

(5) The controller 40 is configured to perform the subjective examination including the RG test to each of the eyes as the subject eye E, and output a command for the binocular balance test after the subjective examination is completed to both of the eyes as the subject eye E. Thus, the binocular balance test can be carried out promptly right after the subjective examination is completed on both eyes.

(6) The controller 40 is configured to verify a cause for the vagueness of the binocular balance based on either the monocular examination of the subject eye E based on the monocular occlusion or the monocular examination of the subject eye E based on the binocular open if the binocular balance is determined to be vague in the binocular balance test with both eyes as the subject eye E simultaneously viewing the optotypes. Thus, an appropriate method can be selected from two types of methods in the binocular balance test so that the cause for the vagueness of the binocular balance can be verified.

(7) The ophthalmologic apparatus 1 further includes an examiner controller 30 configured to receive an input operation from the examiner and output a control signal to the controller 40. The controller 40 is configured to make the objective measurement information into information represented by any one of the two-dimensional coordinates graphs G, G', and G" which indicates the relationship between the objective measurement value (spherical equivalent) and the power of the corrective lens for the subject eye E and/or the subjective measurement time. The controller 40 is further configured to output a command for displaying any one of the two-dimensional coordinates graph G, G', and G" on the display 31 of the examiner controller 30 upon performing the objective monitoring during the RG test. Thus, during the RG test, the examiner can easily determine whether or not the accommodation intervention by the subject eye E has occurred by viewing the two-dimensional coordinates graph G, G', or G" displayed on the examiner controller 30 at hand.

(8) The controller 40 is configured to output, to the examiner controller 30, a command for displaying the objective measurement information at predetermined timing including time intervals when performing the objective monitoring during the RG test. Thus, setting a shorter time interval allows changes in the objective measurement value to be displayed in near real-time on the display 31 of the examiner controller 30. Setting a longer time interval or setting particular timing can reduce the processing load on the controller 40.

(9) The controller 40 is configured to output, to the examiner controller 30, a command for displaying the objective measurement information when the spherical power is changed by the corrective lens during the RG test. The objective measurement information is obtained when the spherical power is changed. Thus, during the RG test, the corresponding two-dimensional coordinates graph including the objective measurement value (spherical equivalent) reflected at the timing of a high possibility of the accommodation intervention by the subject eye E can be presented to the examiner while reducing the processing load of generation of the two-dimensional coordinates graphs G, G', or G".

(10) The controller 40 is configured to output, to the examiner controller 30, a command for displaying the objective measurement information when the voice of the examinee who reads the optotype is recognized during the RG test and/or the weakest power test. The objective measurement information is obtained when the voice is recognized. Thus, during the RG test and/or the weakest power test, the objective measurement value (spherical equivalent) can be reflected in the corresponding two-dimensional coordinates graph at the timing of a high possibility of the accommodation intervention by the subject eye E while reducing the processing load of generation of the two-dimensional coordinates graphs G, G', or G".

The ophthalmologic apparatus according to the first embodiment of the present disclosure has been described. However, the specific configuration of the present disclosure is not limited to the first embodiment. Changes and additions in design should be allowed as long as they do not deviate from the gist of the inventions recited in the claims. The changes and additions in design may include a configuration in which the objective measurement is performed together with the visual acuity measurement with the optotype displayed on the display or the optotype printed on paper or a configuration in which the objective measurement is performed together with the visual acuity measurement with an apparatus having binocularly observable optotypes.

In the first embodiment, the ophthalmologic apparatus 1 serves as the binocular open-field type of ophthalmologic apparatus enabling the individual objective measurement of the eye characteristics of the left and right subject eyes E. However, the ophthalmologic apparatus of the present disclosure is not limited to such an ophthalmologic apparatus and may be a monocular type of ophthalmologic apparatus that measures the eye characteristics of each eye. That is, the ophthalmologic apparatus may include an objective measurement optical system that objectively measures the eye characteristics of the left subject eye E and the eye characteristics of the right subject eye E one by one.

In the first embodiment, as the objective measurement information, exemplarily given are the monitoring display information with the two-dimensional coordinates graph G indicating the relationship between the objective measurement value (spherical equivalent) and the power of the corrective lens for the subject eye E and monitoring display information with the two-dimensional coordinates graph G' or G" indicating the relationship between the objective measurement value (spherical equivalent) and the elapse of time from the start of the subjective examination. However, the objective measurement information is not limited to the information with such a two-dimensional coordinates graph. For example, the information may be monitoring display information in which the spherical equivalent is numerically displayed and the color is changed if a change in a numerical value is not less than a threshold. Sound information (information regarding presence or absence of accommodation intervention) may be added to the graphical monitoring display information or the numerical monitoring display information.

In the first embodiment, during the RG test, a command for monitoring display of the objective measurement information is output to the examiner controller 30 when the spherical power is changed or when the voice is recognized. However, the timing at which a command for displaying the objective measurement information is output to the examiner controller is not limited to the above timings. For example, during the RG test, a command for monitoring display of the objective measurement information may be continuously output to the examiner controller. Alternatively, during the RG test, a command for displaying the objective measurement information may be output to the examiner controller based on a previously set time interval for example.

What is claimed is:

1. An ophthalmologic apparatus comprising:
   a subjective measurement optical system configured to measure a subjective refractive value of a subject eye;
   an objective measurement optical system configured to measure objective refractive characteristics of the subject eye; and
   a controller configured to control the subjective measurement optical system and the objective measurement optical system,
   wherein the controller is further configured to:
      measure a plurality of objective measurement refractive values of the subject eye by the objective measurement optical system at multiple times in a time series at least between a start and an end of an RG test;
      monitor the objective measurement refractive values measured in the time series; and
      determine that an accommodation intervention has occurred during the RG test when a variation in a lowering direction between the measured objective measurement refractive values exceeds a predetermined threshold.

2. The ophthalmologic apparatus according to claim 1, wherein the ophthalmologic apparatus is an objective measuring machine that comprises a subjective function and comprises the subjective measurement optical system and the objective measurement optical system, and
   wherein the objective measurement optical system comprises a function of simultaneously measuring the objective refractive characteristics of both eyes as the subject eye.

3. The ophthalmologic apparatus according to claim 1, wherein the controller is further configured to:
   issue an alert or give feedback to eye examination content when the accommodation intervention has been determined.

4. The ophthalmologic apparatus according to claim 1, wherein in the subjective measurement optical system, an RG chart is used as an optotype in the RG test, the RG chart comprising a red optotype and a green optotype arranged relative to each other.

5. The ophthalmologic apparatus according to claim 4, wherein the controller is further configured to
   perform a subjective examination comprising the RG test to each eye as the subject eye; and
   output a command for a binocular balance test after the subjective examination is completed to both the eyes as the subject eye.

6. The ophthalmologic apparatus according to claim 5, wherein the controller is further configured to verify a cause for vagueness of binocular balance based on either a monocular examination of the subject eye with monocular occlusion or a monocular examination of the subject eye with binocular open if the binocular balance is determined to be vague in the binocular balance test with both eyes as the subject eye simultaneously viewing the optotypes.

7. The ophthalmologic apparatus according to claim 1, further comprising an examiner controller configured to receive an input operation from an examiner and output a control signal to the controller,
   wherein the controller is further configured to
   make the objective measurement refractive values into information represented by a two-dimensional coordinates graph which indicates a relationship between an objective measurement value and power of a corrective lens for the subject eye and/or subjective measurement time; and
   output a command for displaying the two-dimensional coordinates graph on a display of the examiner controller upon performing the objective monitoring during the RG test.

8. The ophthalmologic apparatus according to claim 7, wherein the controller is further configured to output, to the examiner controller, a command for displaying the objective measurement refractive values at predetermined timing including time intervals when performing the objective monitoring during the RG test.

9. The ophthalmologic apparatus according to claim 8, wherein the controller is further configured to output, to the examiner controller, a command for displaying the objective measurement refractive values when the spherical power is changed by the corrective lens during the RG test, the objective measurement refractive values-being obtained at a timing at which the spherical power is changed.

10. The ophthalmologic apparatus according to claim 8, wherein the controller is further configured to output, to the examiner controller, a command for displaying the objective measurement refractive values when a voice of the examinee who reads an optotype is recognized during the RG test, the objective measurement refractive values being obtained at a timing at which the voice is recognized.

11. The ophthalmologic apparatus according to claim 1, wherein the controller is further configured to change a spherical power of a corrective lens as a measure to reduce the accommodative intervention when the accommodation intervention is determined.

12. The ophthalmologic apparatus according to claim 1, wherein the controller is further configured to provide an instruction to an examiner as a measure to reduce the accommodative intervention when the accommodation intervention is determined.

13. The ophthalmologic apparatus according to claim 1, wherein the objective measurement refractive values are equivalent spherical powers.

14. The ophthalmologic apparatus according to claim 1, further comprising an examiner controller configured to receive an input operation from an examiner and output a control signal to the controller, wherein the examiner controller is configured to display a two-dimensional coordinates graph in which a plurality of objective measurement refractive values obtained between the start and the end of the RG test are plotted.

15. The ophthalmologic apparatus according to claim 14, wherein the controller is further configured to determine that the accommodative intervention has occurred when the plotted objective measurement refractive values exhibit a variation in a lowering direction that exceeds a predetermined threshold.

* * * * *